(12) United States Patent
Friedman et al.

(10) Patent No.: US 9,063,063 B2
(45) Date of Patent: Jun. 23, 2015

(54) LOW-DIMENSIONAL MATERIAL CHEMICAL VAPOR SENSORS

(71) Applicants: Adam L. Friedman, Silver Spring, MD (US); F. Keith Perkins, Alexandria, VA (US); Enrique Cobas, Capitol Heights, MD (US); Paul M Campbell, Alexandria, VA (US); Glenn G. Jernigan, Waldorf, MD (US); Berend T Jonker, Davidsonville, MD (US)

(72) Inventors: Adam L. Friedman, Silver Spring, MD (US); F. Keith Perkins, Alexandria, VA (US); Enrique Cobas, Capitol Heights, MD (US); Paul M Campbell, Alexandria, VA (US); Glenn G. Jernigan, Waldorf, MD (US); Berend T Jonker, Davidsonville, MD (US)

(73) Assignee: The United States of America, as represented by the Secretary of the Navy, Washington, DC (US)

(*) Notice: Subject to any disclaimer, the term of this patent is extended or adjusted under 35 U.S.C. 154(b) by 0 days.

(21) Appl. No.: 14/075,840

(22) Filed: Nov. 8, 2013

(65) Prior Publication Data
US 2014/0273259 A1 Sep. 18, 2014

Related U.S. Application Data

(60) Provisional application No. 61/788,610, filed on Mar. 15, 2013.

(51) Int. Cl.
*G01N 27/12* (2006.01)
*G01N 27/02* (2006.01)
*G01N 27/00* (2006.01)
*G01N 33/00* (2006.01)
*B82Y 15/00* (2011.01)

(52) U.S. Cl.
CPC ............. *G01N 27/125* (2013.01); *B82Y 15/00* (2013.01); *G01N 33/0057* (2013.01); *Y10T 29/49117* (2015.01); *Y10T 436/174614* (2015.01); *G01N 33/0027* (2013.01); *Y10T 436/173845* (2015.01); *Y10T 436/17* (2015.01); *G01N 27/02* (2013.01); *G01N 33/0036* (2013.01)

(58) Field of Classification Search
CPC ..... G01N 27/125; G01N 27/12; G01N 27/04; G01N 27/00; G01N 33/0057; G01N 33/0036; G01N 33/0027; G01N 33/0009; G01N 33/0004; G01N 33/00; B82Y 15/00; Y10T 436/174614; Y10T 436/173845; Y10T 436/17; Y10T 436/00
USPC ................. 436/112, 111, 106, 156, 151, 149; 422/98, 83, 50
See application file for complete search history.

(56) References Cited

PUBLICATIONS

Perkins F.K. et al, Chemical Vapor Sensing with Monolayer MoS2, Nano Letters, Jan. 22, 2023, vol. 13, p. 668-673.*
Radisavljevic B., et al, Single-layer MoS2 transistors, Nature Nanotechnology, Jan. 30, 2011, vol. 6, pp. 147-151.*
Sanchez, Oriol Lopez, Single-layer Molybdenum disulfide photodetectors, Feb. 2012, Ecole Polytechnique Federale de Lausanne, p. 1-65.*

* cited by examiner

*Primary Examiner* — Christine T Mui
(74) *Attorney, Agent, or Firm* — US Naval Research Laboratory; Stephen T. Hunnius (57) ABSTRACT

A method of making a low-dimensional material chemical vapor sensor comprising exfoliating $MoS_2$, applying the monolayer flakes of $MoS_2$ onto a $SiO_2$/Si wafer, applying a methylmethacrylate (MMA)/polymethylmethacrylate (PMMA) film, defining trenches for the deposition of metal contacts, and depositing one of Ti/Au, Au, and Pt in the trench and resulting in a $MoS_2$ sensor. A low-dimensional material chemical vapor sensor comprising monolayer flakes of $MoS_2$, trenches in the $SiO_2$/Si wafer, metal contacts in the trenches, and thereby resulting in a $MoS_2$ sensor. A full spectrum sensing suite comprising similarly fabricated parallel sensors made from a variety of low-dimensional materials including graphene, carbon nanotubes, $MoS_2$, BN, and the family of transition metal dichalcogenides. The sensing suites are small, robust, sensitive, low-power, inexpensive, and fast in their response to chemical vapor analytes.

9 Claims, 5 Drawing Sheets

LOW-DIMENSIONAL MATERIAL CHEMICAL VAPOR SENSORS

REFERENCE TO RELATED APPLICATION

This application is a non-provisional of, and claims priority to and the benefits of, U.S. Provisional Patent Application No. 61/788,610 filed on Mar. 15, 2013, the entirety of which is herein incorporated by reference.

BACKGROUND

This disclosure demonstrates that single atomic layer $MoS_2$ can be used in chemical vapor sensors and that the response is selective to analytes that are strong electron donors and some polar molecules.

This disclosure demonstrates that the response of the $MoS_2$ chemical sensors nicely complements the response to sensors fabricated from graphene and carbon nanotube (CNT) meshes. In particular, when combined, the three materials can provide a sensing suite that can correctly identify triethylamine (TEA) and acetone vapors.

Furthermore, this disclosure concerns a new type of chemical sensor created from a variety of low-dimensional materials including but not limited to graphene, carbon nanotubes, and monolayer forms of a variety of transition metal dichalcogenides that will be able to accurately identify with great sensitivity and precision a variety of airborne chemicals of interest.

The planar habit of two-dimensional (2D) materials is attractive for the ultimate size scaling of many types of devices, offers relative ease of fabrication, the requisite large-scale integration, and exceedingly low power consumption.

The very high surface-to-volume ratio of such single or few monolayer materials enables highly efficient gating of charge transport via surface gates, obviating the need for the more complex growth and fabrication procedures, and offers an enormous functional area per volume for chemical sensing applications.

Graphene has captivated the attention of the scientific community since the first measurements of high mobility transport were reported in single layer flakes. Recent effort has focused on other 2D materials such as the transition metal dichalcogenides, and field effect transistors with a monolayer of $MoS_2$ as the active channel were shown to exhibit high on/off ratios at room temperature, ultra-low standby power dissipation and well-defined photoresponse.

The high surface-to-volume ratio is also important for new sensor materials, which must exhibit selective reactivity upon exposure to a range of analytes (determined by the character of surface physisorption sites), rapid response and recovery, and sensitive transduction of the perturbation to the output parameter measured.

The conductivity of graphene near the charge neutrality point has been shown to change with adsorption of a variety of analytes, but annealing to 150° C. was required to restore the conductivity to its original value, suggesting the analytes were strongly bound. Other work has shown that graphene's intrinsic response to physisorption of analytes such as ammonia is very small. The sensitivity can be enhanced by functionalizing the graphene surface, e.g. by oxidation, but these devices showed little selectivity, and functionalization introduces additional complexity to the fabrication process.

Recent work has shown that measuring analyte-dependent changes in the low frequency noise spectrum can enhance the selectivity of graphene sensors, although degassing in vacuum at room temperature for several hours between measurements was needed to obtain good reproducibility. Other 2D materials are likely to offer selective surface reactivity to physisorbed species, and if semiconducting in character, can provide both lower background carrier densities and the possibility of photo-modulated sensing mechanisms. Furthermore, in the past it has been shown that 1-dimensional (1D) CNTs are quite responsive to a variety of analytes, although their response is also not selective.

Due to the wide variety of available low-dimensional materials, each having its own unique chemistry and electronic properties, we designed a new class of full-spectrum chemical sensors that are able to selectively and sensitively respond to a wide variety of analytes by combining the sensing properties of each low-dimensional material in parallel.

By combining the responses from each low-dimensional material, we can positively identify chemicals of interest with a never-before-seen accuracy.

Furthermore, because these materials are atomic-scaled (for instance, graphene is ~3 Angstroms thick, $MoS_2$ is ~6 Angstroms thick), these full-spectrum sensor suites can be integrated into applications demanding the smallest of space restrictions, and address system integration issues. Additionally, as two terminal low-dimensional devices require very low currents (~nA) for successful operation, these sensor suites can be integrated into applications demanding ultra-low power electronics. Moreover, due to the atomic size and enormous surface to volume ratio of the low-dimensional films, any small adsorbate will cause an immediate electrical response, making these sensors incredibly fast to react to vapor analytes. The combination of sensitivity, versatility, atomic size, low-power, high reaction speed, and low cost of fabrication make these low-dimensional sensing suites superior to any other chemical vapor sensor currently on the market, which usually emphasizes only one or two of these advantageous qualities.

SUMMARY OF DISCLOSURE

Description

This disclosure concerns a new type of chemical sensor created from a variety of low-dimensional materials including but not limited to graphene, carbon nanotubes, and monolayer forms of a variety of transition metal dichalcogenides that will be able to accurately identify with great sensitivity and precision a variety of airborne chemicals of interest.

This disclosure concerns a new class of full-spectrum chemical sensors that are able to selectively and sensitively respond to a wide variety of analytes by combining the sensing properties of each low-dimensional material in parallel. By combining the responses from each low-dimensional material, we can positively identify chemicals of interest with a never-before-seen speed and accuracy.

DESCRIPTION OF THE DRAWINGS

The following description and drawings set forth certain illustrative implementations of the disclosure in detail, which are indicative of several exemplary ways in which the various principles of the disclosure may be carried out. The illustrated examples, however, are not exhaustive of the many possible embodiments of the disclosure. Other objects, advantages and novel features of the disclosure will be set forth in the following detailed description when considered in conjunction with the drawings.

FIG. 1(a) is a schematic of a single monolayer of $MoS_2$ that is supported on an $SiO_2/Si$ substrate and contacted with Au contact pads. Transient physisorption of molecules induces temporary changes in the conductivity of the monolayer channel. (b) An optical image of the processed devices showing the monolayer $MoS_2$ flakes electrically contacted by multiple Au leads.

FIG. 2 is an illustration of an example of a $MoS_2$ sensor response to TEA. The blue dashed line shows the analyte exposure pulse sequence as a percent of the equilibrium vapor pressure ($P_0$). The red line shows the response to nitrogen flow changes only, giving a baseline for the sensor. The black line shows the conductance response to the TEA measured as a percentage of the conductance G at time=0 ($G_0$).

DETAILED DESCRIPTION OF THE INVENTION

This disclosure demonstrates that single atomic layer $MoS_2$ can be used in chemical vapor sensors and that the response is selective to analytes that are strong electron donors and some polar molecules.

This disclosure demonstrates that the response of the $MoS_2$ chemical sensors nicely complements the response of sensors fabricated from graphene and carbon nanotube (CNT) meshes. In particular, when combined, the three materials can provide a sensing suite that can correctly identify triethylamine (TEA) and acetone vapors.

Furthermore, this disclosure concerns a new type of chemical sensor created from a variety of low-dimensional materials including but not limited to graphene, carbon nanotubes, and monolayer forms of a variety of transition metal dichalcogenides that will be able to accurately identify with great sensitivity and precision a variety of airborne chemicals of interest.

Example 1

$MoS_2$ is mechanically exfoliated onto $SiO_2$/Si wafers.

Monolayer flakes are identified with a combination of optical inspection, atomic force microscopy (AFM), and Raman Spectroscopy.

Electron beam lithography with a methylmethacrylate (MMA)/polymethylmethacrylate (PMMA) layer is used to define trenches in the layer for the deposition of patterned metal contacts to the $MoS_2$ film.

Ti/Au, Au, or Pt is deposited in the trenches by electron beam evaporation.

Similar sensor devices are made using the same methods with chemical vapor deposition (CVD) grown semiconducting single walled CNT meshes and CVD grown monolayer graphene films. The sensors are mounted into a specially built chemical sensor testing apparatus and contacts are made to the sensors using microprobe positioners.

Nitrogen gas is bubbled through a select liquid analyte and sensors are exposed to the mixture, with the concentration of analyte in the mixture controlled using a solenoid valve and monitored with a residual gas analyzer.

The sensors are exposed to a variety of analytes and the electrical resistance is measured using a 2-terminal contact configuration.

Figure 2:
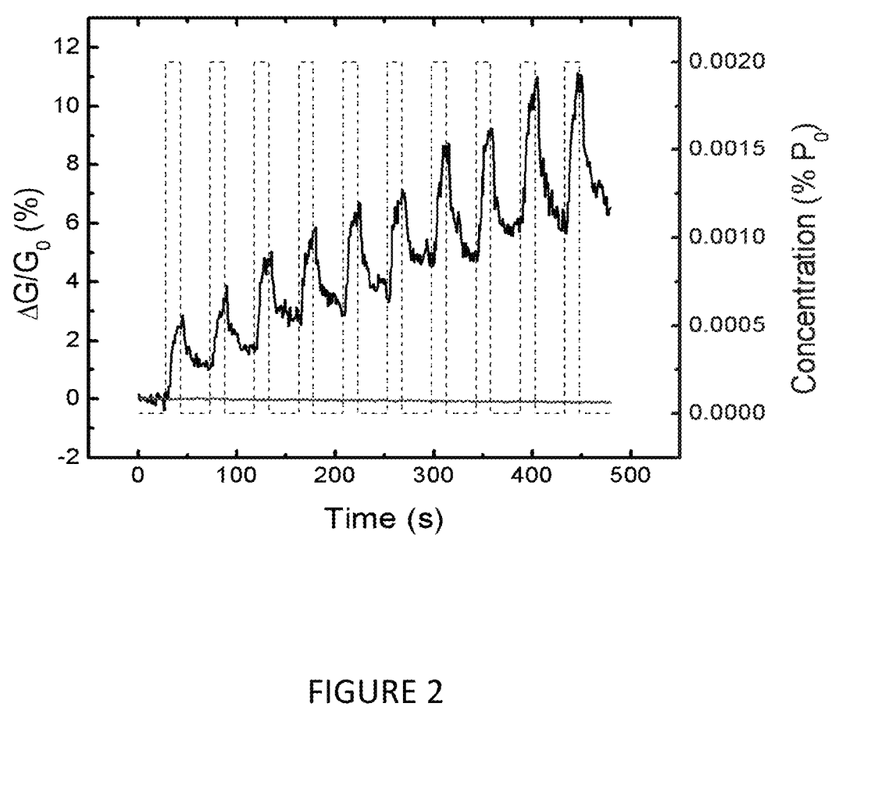

A functional sensor exhibits a rising and falling resistance that mirrors the pulsing of the analyte exposure. This is shown in FIG. 2.

Figure 3:
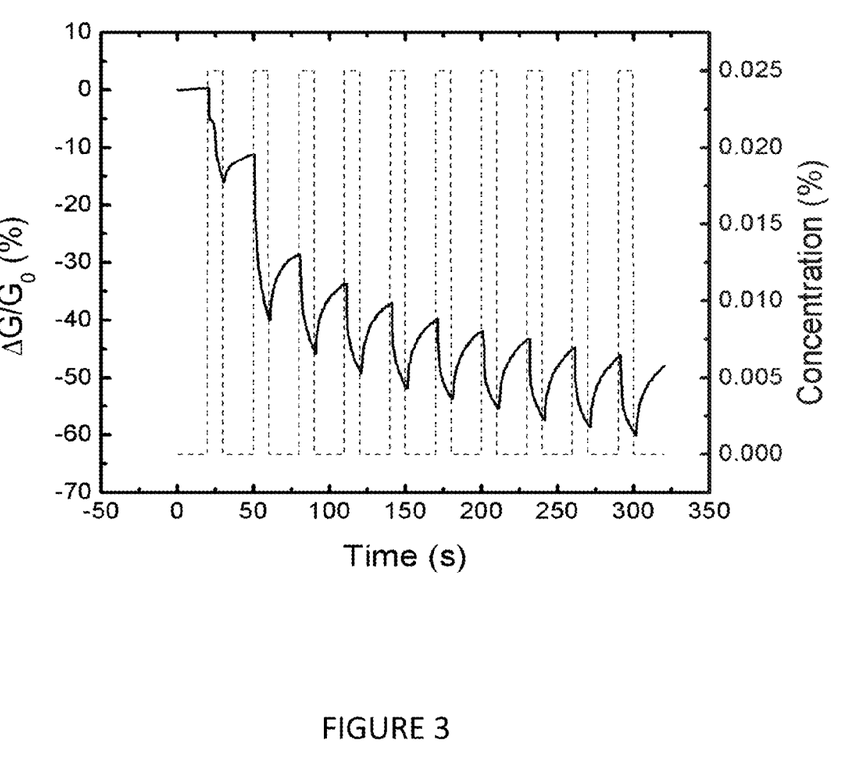
FIG. 3 is a graph showing the CNT response to TEA (black line) with the analyte pulse sequence visible in the blue dashed line. The result is complementary to $MoS_2$ because it gives a negative conductance for the positive conductance seen in $MoS_2$.
Figure 4:
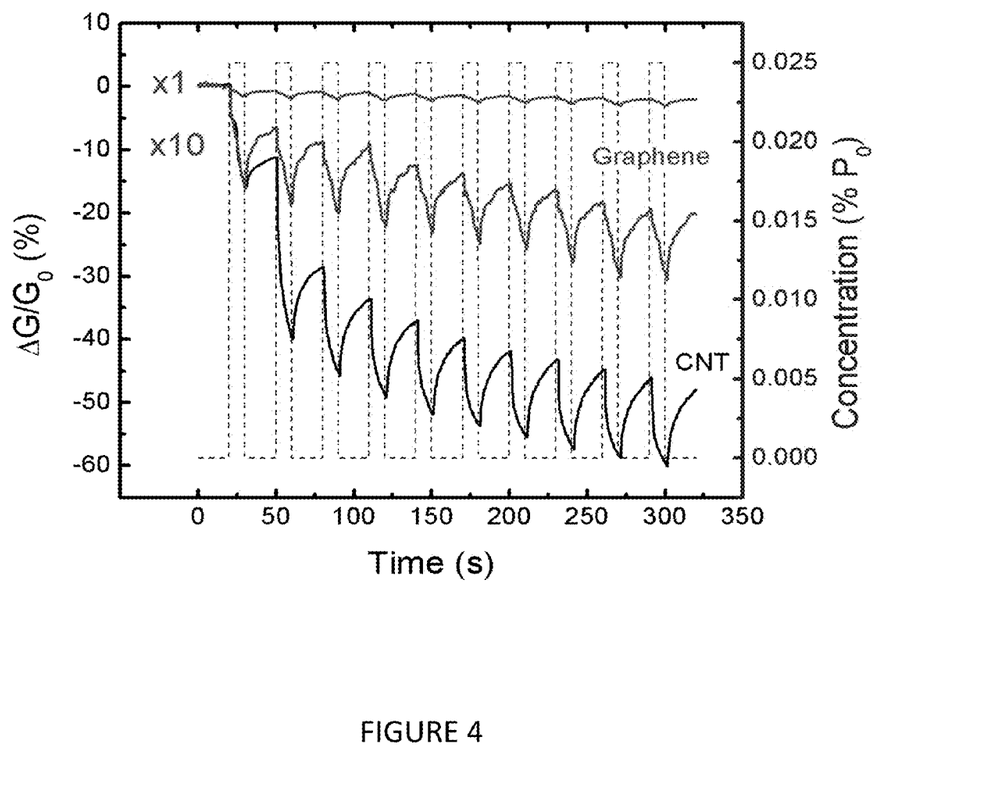
FIG. 4 is a graph showing a comparison of the CNT response to the graphene response. ×1 indicates the raw graphene data, while ×10 indicates the data has been multiplied by 10 to make comparison easier.

FIG. 3 shows a comparison of the $MoS_2$ sensor with CNT and graphene sensors.

We find that while carbon nanotube meshes are not selective to any particular analyte, showing a sensitive negative resistance response, $MoS_2$ sensors are extremely selective to strong electron donors, such as TEA, and highly polar molecules, such as acetone.

When combined, CNT/$MoS_2$ sensors correctly identify these molecules.

Graphene, while neither as selective nor as sensitive a sensor as carbon nanotubes or $MoS_2$, when combined into the sensor allows a third method of analyte identification.

Figure 5:
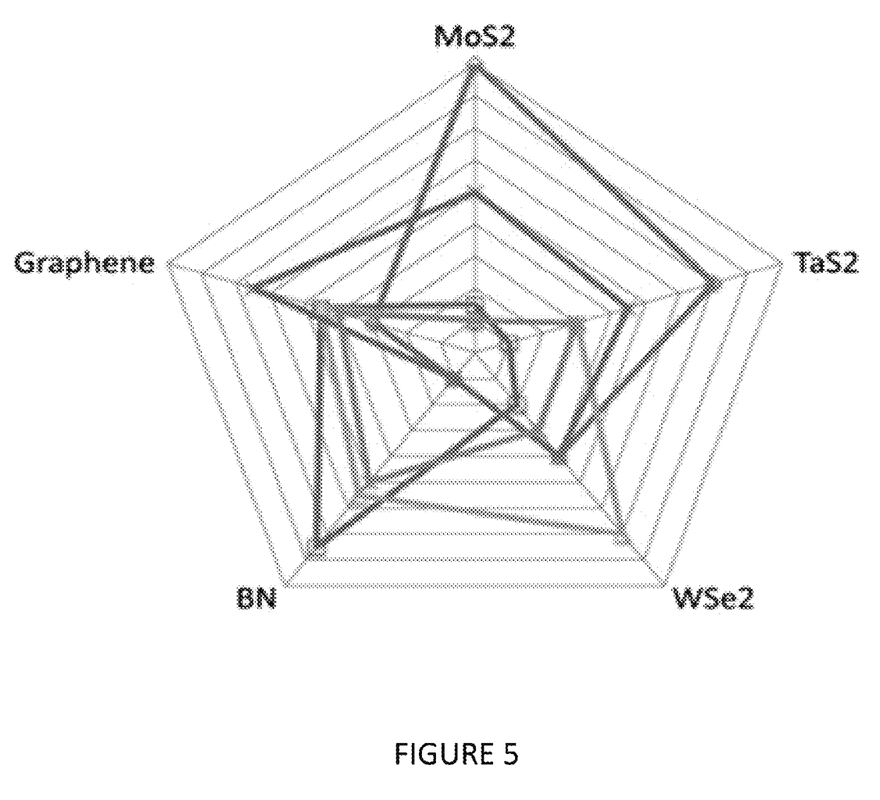
FIG. 5 is a radar plot showing the possible response (data is hypothetical) of a suite of low dimensional materials as a full spectrum sensor, in which the distance from the origin indicates the relative sensitivity to a particular analyte of a variety materials, each located at its particular node on the perimeter. The combination of different responses from a variety of materials allows for more accurate identification and detection of analytes than ever before.

There exists a whole class of materials in the transition metal dichalcogenide family that are accessible in monolayer format that when further combined into the sensor suite provide an unparalleled ability to sense and identify a wide variety of analytes with great precision and accuracy. Some other examples are illustrated in FIG. 5.

Example 2

Figure 1:
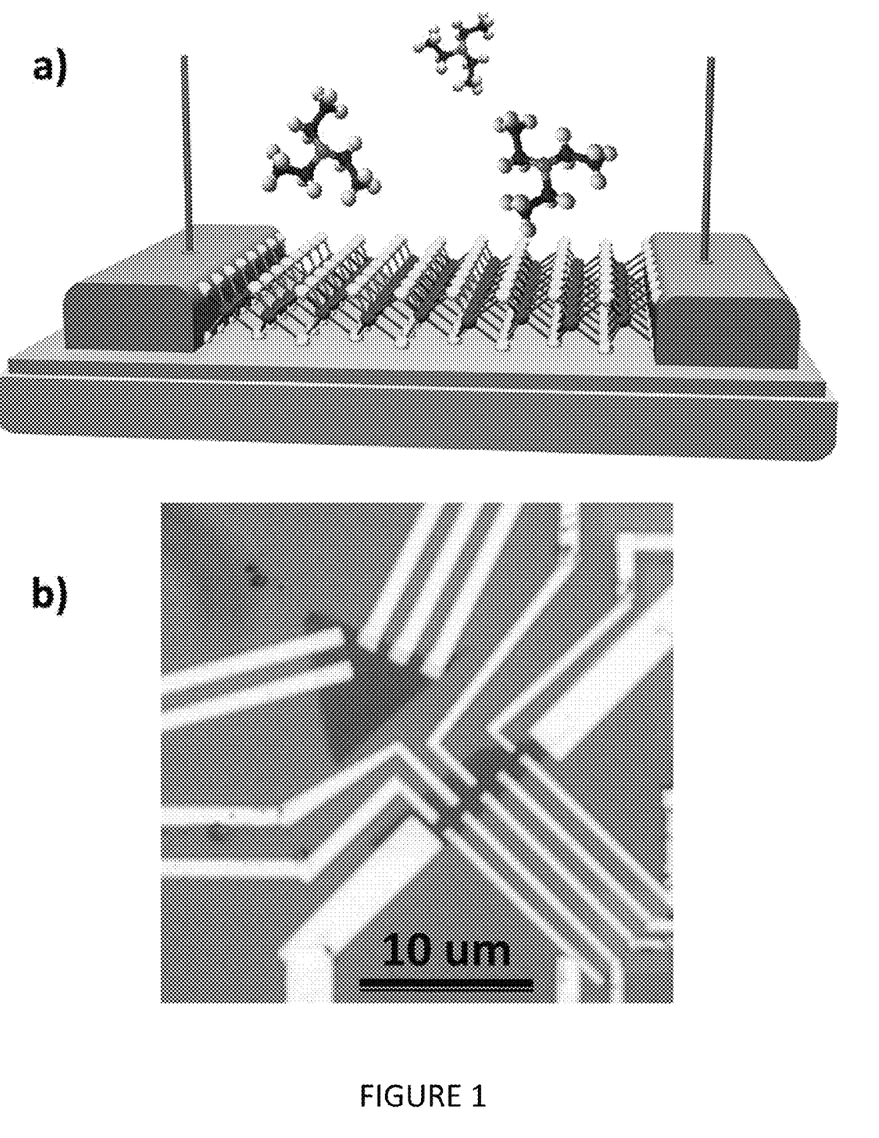

$MoS_2$ is a layered compound with weak interaction between the layers, similar to graphite, and is widely used as a lubricant. Each layer consists of a plane of molybdenum atoms sandwiched between layers of sulfur atoms as shown in FIG. 1(a). It is relatively nonreactive at moderate temperatures (<350° C.)—it is difficult to oxidize and unaffected by dilute acids. In contrast with graphite/graphene, it is a semiconductor with an indirect bandgap (1.2 eV) and exhibits catalytic properties useful for hydrodesulfurization.

Recent work has shown that a single monolayer of $MoS_2$ exhibits properties markedly different from the bulk: it transitions from an indirect to direct gap semiconductor (~1.9 eV) with high luminescence efficiency and can be used as the transport channel in a field effect transistor with high on/off ratio and pronounced photoresponse.

Our sensor devices were fabricated from monolayer flakes of $MoS_2$ that were exfoliated from bulk samples using the "Scotch tape" method and deposited onto a 270 nm thick thermal $SiO_2$ film on Si wafers.

Electrical contacts were placed on the $MoS_2$ flake by liftoff processes using electron beam lithography followed by electron beam evaporation of Au and Ti/Au.

An image of a typical sensor device is shown in FIG. 1(b). The bulk samples were obtained from three different sources, and the responsivity of the sensor flakes showed some variability that we attribute to variations in the purity of the original bulk samples.

The electrical response to vapor exposure of a selected analyte was evaluated in a combined probe station/gas bubbler dosing system.

The gas flow, analyte concentration, and analyte pulse sequence are controlled by computer via appropriate mass flow controllers and valves.

The analyte concentration is recorded as a percent of its equilibrium vapor pressure at 20° C., $P_0$. The sample conductivity is continuously measured using standard lock-in amplifier techniques while a timed sequence of analyte pulses of selected concentration are introduced into the 5 lpm $N_2$ carrier gas stream.

The data are presented as a change in conductivity, $\Delta G/G_0$, versus time, where $G_0$ is the initial conductivity when the pulse sequence is begun. All data are obtained at room temperature and ambient pressure.

The sensor response was measured for a variety of analytes, including those considered to be electron donors, acceptors, or highly polar molecules.

The $MoS_2$ monolayer sensor exhibits a pronounced response to triethylamine (TEA-$N(CH_2$—$CH_3)_3$) exposure, a laboratory-safe decomposition product from the V-series nerve gas agents. The response to a sequence of 10 TEA pulses, each with a concentration of 0.002% $P_0$ (~1 ppm), was recorded. The TEA is on for 15 s and off for 30 s (within the constant 5 lpm $N_2$ carrier flow).

Upon exposure to TEA, the $MoS_2$ conductivity increases abruptly, with an initially rapid rise (~5 s) followed by a slower approach to saturation. This initial response is much more rapid than the 30 s reported previously for multilayer $MoS_2$. Single pulse measurements at 0.02% $P_0$ (10 ppm) show that the response saturates at exposure times of ~60 s for this concentration.

When the TEA is turned off, the conductivity shows the reverse behavior, with an initially rapid 5 s decrease and a slower approach to baseline. These sawtooth responses were recorded and we attribute it to charge accumulation.

A control measurement with no TEA in the pulsed gas sequence exhibits no change in conductivity, confirming that the observed response is due to interaction of the $MoS_2$ with TEA and not to changes in gas flow or residual contaminants in the $N_2$ carrier gas or in the plumbing of the dosing system.

A second control measurement showed that the monolayer $MoS_2$ sensor exhibited no response to water vapor (0.025% $P_0$~6 ppm), a desirable characteristic, while a monolayer graphene sensor (purple curve) shows a pronounced response to this ubiquitous background constituent.

The amplitude of the conductivity change increases with increasing TEA concentration. The device response to a sequence of pulses in which the TEA concentration increases from 0.002% $P_0$ (1 ppm) to 0.2% $P_0$ (100 ppm) over a total pulse sequence of 450 s. The conductivity change with each TEA pulse exhibits similar characteristics as noted above, with an initially rapid rise and fall and a positively sloped background. The strong response and excellent signal-to-noise provide a TEA detection threshold of 10 ppb, which is a sensitivity that is better than or on par with all current commercially available TEA sensors.

Example 3

For comparison, similar data were acquired for planar sensors fabricated from (a) monolayer graphene grown by chemical vapor deposition on copper and (b) a carbon nanotube (CNT) network consisting of a dense array of CNTs forming an electrically continuous thin film, as the transport/sensor channel.

These data were recorded where $\Delta G/G_0$ is plotted for a sequence of TEA pulses (10 s on, 20 s off) of 0.025% $P_0$ (12 ppm) concentration. The CNT response amplitude to a single pulse is comparable to that of the $MoS_2$ monolayer, while that of the graphene sensor is much smaller.

However, in marked contrast with the response exhibited by the $MoS_2$, the graphene and CNT conductivity both decrease with TEA exposure, and the data are superposed on a negatively sloped background.

The opposite response of the $MoS_2$ and graphene/CNT sensors can be understood to first order by considering the transient charge perturbation to the sensor material upon interaction with the TEA molecule. Our $MoS_2$ monolayer samples are n-type, while the air-exposed CNT networks exhibit a p-type character, and the graphene device as fabricated possesses a Dirac point at a substantial positive substrate bias indicating that the dominant carriers are holes. TEA is a strong electron donor, and thus transient physisorption will enhance the majority carrier density and conductivity for $MoS_2$ but decreases these parameters on graphene and the CNT network.

The opposite response of the $MoS_2$ and graphene/CNT devices to TEA exposure provides a strong indicator of TEA presence with high confidence.

In the following paragraphs, we make a comparison to the CNT network devices, because they have been shown to be highly sensitive to a wide variety of analytes.

Example 4

The response of the $MoS_2$ sensor to analytes considered to be weak donors was correspondingly weaker.

For example, exposure to tetrahydrofuran, $(CH_2)_4O$, produced only a modest response (<10%), while exposure to dimethylformamide, $(CH_3)_2NC(O)H$, produced no response above the noise level.

Example 5

The response and sensitivity of the $MoS_2$ monolayer to other classes of analytes was determined in a similar fashion.

The response to a pulse sequence of acetone $(CH_3)_2CO$, a highly polar molecule, was recorded, where the acetone concentration increases from 0.02% $P_0$ (50 ppm) to 2% $P_0$ (5000 ppm).

The conductivity again increases upon exposure, with temporal characteristics similar to those observed for TEA—the incremental change in conductivity is strongly correlated with the exposure pulse sequence, the amplitude of $\Delta G/G_0$ is comparable for a given concentration, and the background exhibits a positive slope over the total duration of the exposure.

The sensitivity to acetone is much lower than for TEA, with a detection threshold of 500 ppm, although this sensitivity is sill better than or on par with all current commercially available acetone vapor sensing devices.

The corresponding response of a CNT network sensor exhibits a complementary response consistent with the transient charge perturbation model discussed above: the incremental conductivity decreases with acetone exposure, and the background exhibits a negative slope.

Example 6

In contrast with the relatively strong responses described above, the $MoS_2$ sensor exhibited no measurable change in conductivity upon exposure to analytes considered to be electron acceptors, including o-dichlorobenzene, 1,5-dichloropentane, o-nitrotoluene, and nitromethane at concentrations as high as 2% $P_0$ ($P_0$=1350, 960, 136, and 37 400 ppm, respectively), although the CNT devices respond to all.

We note, however, that transport in CNTs is also affected by dipole-induced scattering, a mechanism that would only decrease conductivity, and may not be relevant for 2D materials such as $MoS_2$, where some degree of charge screening can occur.

Thus the $MoS_2$ sensor exhibits a much higher degree of selectivity than the CNT-based sensors, a desirable sensor characteristic.

As an example, the response to a sequence of nitrotoluene (NT) pulses, a laboratory-safe simulant for the explosive trinitrotoluene (TNT), was recorded. As the NT concentration increases from 0.01% $P_0$ to 1% $P_0$, no change in conductivity of the $MoS_2$ monolayer is visible. The corresponding response of the CNT network sensor was compared, with the CNT conductivity increasing significantly upon exposure.

The sensitivity and selectivity of both the monolayer $MoS_2$ and CNT network sensors to these various analytes was compared.

The $MoS_2$ monolayer sensor displays good sensitivity, high selectivity, and a response that is typically opposite in polarity to that of CNT networks.

While the states responsible for the $MoS_2$ in-plane conductivity derive from the sulfur-molybdenum hybridized orbitals, we suggest that the interaction mechanism with the analyte is mediated by the localized lone pair orbitals of the sulfur end units. Others have modeled the atomic orbital configuration for planar $MoS_2$ sheets to understand the process of hydrodesulfurization. They found that the Mo $3d_{xy}$ orbitals are used to form the Mo—S bond. The Mo $3d_{yz}$ orbitals and S 2p orbitals extend above the surface plane and are free to interact—the charge density distributions make the Mo $3d_{yz}$ slightly reduced (negatively charged) and the S 2p slightly oxidized (positively charged). It is this polarized surface that attracts the other plane of $MoS_2$ in the bulk layered structure.

Other 2D materials ($TaS_2$, $WSe_2$, $WS_2$, $MoTe_2$, $MoSe_2$, $NbSe_2$, $MgB_2$, BN, etc.) offer complementary sensitivity due to different chemical composition and bonding. Suites of these 2D material sensors and carbon nanotubes with complementary responsivities can be utilized, integrated with transistor amplifiers fabricated from the same materials, enabling unambiguous identification of a wide range of analytes in a very compact and low power package.

Example 7

Planar devices were fabricated from $MoS_2$ exfoliated monolayer flakes using the "Scotch tape" method deposited onto a 270 nm thermal $SiO_2$ film on n-type Si wafers.

Optical contrast and Raman spectroscopy were used to identify and confirm the monolayer areas used for subsequent processing.

After optical inspection of the wafers in a microscope and isolation of suspected monolayers, atomic force microscopy measurements were performed to ensure accurate monolayer selection (1 ML~0.7 nm).

Raman data and photoluminescence spectra analysis also confirm that the samples were single monolayer.

Ti/Au bond-pad contacts were formed by e-beam lithography using MMA/PMMA resist and metal evaporation and lift-off in acetone.

A second e-beam lithography step/metal evaporation/lift-off is performed to connect the $MoS_2$ to the bond pads with an Au contact line.

Excess $MoS_2$ near the device is removed by defining a mesa level with another electron beam lithography step and then reactive ion etching in $SF_6/O_2$.

A combined electrical probe station-gas bubbler system was used to determine the electrical response of the sensor samples to controlled exposures of various analytes.

Dry $N_2$ is bubbled at controlled low flow rates (milliliters per minute) by means of a glass frit through a container of liquid analyte with an equilibrium vapor pressure $P_0$ (at 20° C.). It is expected that the $N_2$ stream leaving the bubbler is saturated with analyte vapor. This vapor stream is diluted by mixing with a constant flow of 200 mlpm dry $N_2$. Actual concentration of analyte is checked in a residual gas analyzer equipped with a capillary and differential pumping to achieve operation at atmospheric pressure (Hiden Analytical Inc. HPR-20 QIC). This diluted vapor stream is switched into a much larger 5 lpm $N_2$ flow by means of a solenoid-activated valve to create a gas of controlled high dilution.

This gas stream is directed at the sample under test from a separation of a few millimeters.

Electrical contact to the sample pads is provided through Au-coated tungsten probe tips, and the conductivity between two contacts on the $MoS_2$ is measured by applying a small AC voltage (~100 mVAC RMS, 1 kHz) to one electrode while observing the voltage drop across a bias resistor between another electrode and ground with a lock-in amplifier. The value of the bias resistor is selected to approximately match the nominal impedance of the $MoS_2$ channel. In this way we measured resistance with a high signal-to-noise ratio.

The complementary properties of the large family of transition metal dichalcogenides and low-dimensional materials, such as graphene and CNTs, offers a never before seen ability to selectively respond to a wide variety of analytes in the same sensor device.

Moreover, because these materials exhibit these properties in single atomic layer format, these new chemical sensors are used in applications with smallest of available space as a requirement.

These chemical sensors are also inherently fully flexible, adding to the variety of situations where they can be deployed.

These low dimensional sensors have also shown temperature stability from cryogenic temperatures to well above room temperature.

No other class of sensors takes full advantage of low-dimensional materials to provide both a high sensitivity and selective response to a variety of chemical vapors.

The above examples are merely illustrative of several possible embodiments of various aspects of the present disclosure, wherein equivalent alterations and/or modifications will occur to others skilled in the art upon reading and understanding this specification and the annexed drawings. In addition, although a particular feature of the disclosure may have been illustrated and/or described with respect to only one of several implementations, such feature may be combined with one or more other features of the other implementations as may be desired and advantageous for any given or particular application. Also, to the extent that the terms "including", "includes", "having", "has", "with", or variants thereof are used in the detailed description and/or in the claims, such terms are intended to be inclusive in a manner similar to the term "comprising".

What we claim is:

1. A method of making a low-dimensional material chemical vapor sensor comprising:
   exfoliating $MoS_2$;
   identifying monolayer flakes of $MoS_2$;
   applying the monolayer flakes of $MoS_2$ onto a $SiO_2$/Si wafer;

applying a methylmethacrylate (MMA)/polymethylmethacrylate (PMMA) film;
utilizing electron beam lithography and defining trenches in the film for the deposition of patterned metal contacts to the $MoS_2$; and
depositing one selected from the group consisting of Ti/Au, Au, and Pt in the trench by utilizing electron beam evaporation and resulting in a $MoS_2$ sensor.

2. The method of making a low-dimensional material chemical vapor sensor of claim 1 further comprising:
mounting the $MoS_2$ sensor in a chemical sensor testing apparatus;
mounting a chemical vapor deposition (CVD) grown semiconducting single walled CNT mesh in the chemical sensor testing apparatus;
mounting a CVD grown monolayer graphene films in the chemical sensor testing apparatus; and
making contacts to the sensors using tungsten microprobe positioners.

3. A low-dimensional material chemical vapor sensor comprising:
monolayer flakes of $MoS_2$;
the monolayer flakes of $MoS_2$ applied to a $SiO_2$/Si wafer;
trenches in the $SiO_2$/Si wafer;
metal contacts in the trenches;
and thereby resulting in a $MoS_2$ sensor.

4. The low-dimensional material chemical vapor sensor of claim 3 wherein the metal contacts are selected from the group consisting of Ti/Au, Au, and Pt.

5. The low-dimensional material chemical vapor sensor of claim 4 further comprising:
a chemical sensor testing apparatus to house the $MoS_2$ sensor.

6. The low-dimensional material chemical vapor sensor of claim 5 further comprising:
a chemical vapor deposition (CVD) grown semiconducting single walled CNT mesh in the chemical sensor testing apparatus;
a CVD grown monolayer graphene films in the chemical sensor testing apparatus; and
electrical contacts to the sensors.

7. The low-dimensional material chemical vapor sensor of claim 6 wherein the monolayer flakes of $MoS_2$ are substituted for by monolayer flakes of another transition metal dichalcogenide.

8. A method of chemical vapor testing comprising:
bubbling nitrogen gas through a first select liquid analyte and forming a vapor;
exposing a low-dimensional material chemical vapor sensor to the vapor containing the analyte;
monitoring the concentration of the analyte using a solenoid valve and a residual gas analyzer; and
measuring the electrical resistance using a 2-terminal contact configuration.

9. The method of chemical vapor testing of claim 8 further comprising:
bubbling nitrogen gas through a second select liquid analyte;
exposing the low-dimensional material chemical vapor sensor to the second analyte;
monitoring the concentration of the second analyte using a solenoid valve and a residual gas analyzer; and
measuring the electrical resistance using a 2-terminal contact configuration.

* * * * *